United States Patent [19]

Aber

[11] Patent Number: 5,957,672

[45] Date of Patent: Sep. 28, 1999

[54] BLOOD PUMP BEARING SYSTEM

[75] Inventor: Gregory S. Aber, Houston, Tex.

[73] Assignee: The United States of America as represented by the Administrator of the National Aeronautics and Space Administration, Washington, D.C.

[21] Appl. No.: 08/664,579

[22] Filed: Jun. 17, 1996

Related U.S. Application Data

[63] Continuation-in-part of application No. 08/153,595, Nov. 10, 1993, Pat. No. 5,527,159, and a continuation-in-part of application No. 08/451,709, May 26, 1995, Pat. No. 5,678,306.

[51] Int. Cl.⁶ .................................................. F04B 35/04
[52] U.S. Cl. ................. 417/423.12; 417/356; 384/907.1
[58] Field of Search ..................... 417/355, 356, 417/423.12; 384/246, 245, 244, 907.1, 913

[56] References Cited

U.S. PATENT DOCUMENTS

| 1,424,804 | 8/1922 | Day ........................................... 33/364 |
| 1,440,059 | 12/1922 | Colomb .................................... 368/324 |
| 1,950,867 | 3/1934 | Straumann ............................... 308/159 |
| 1,975,646 | 10/1934 | Luthy ....................................... 308/159 |
| 2,085,751 | 7/1937 | Holtz ....................................... 308/159 |
| 2,111,629 | 3/1938 | Holtz ....................................... 308/159 |
| 4,135,253 | 1/1979 | Reich et al. ................................ 3/1.7 |
| 4,382,199 | 5/1983 | Isacson ...................................... 310/87 |
| 4,507,048 | 3/1985 | Belenger et al. .......................... 415/90 |
| 4,625,712 | 12/1986 | Wampler .................................. 182/1 D |
| 4,688,998 | 8/1987 | Olsen et al. .............................. 417/356 |
| 4,763,032 | 8/1988 | Bramm et al. .......................... 310/90.5 |
| 4,779,614 | 10/1988 | Moise ....................................... 600/16 |
| 4,797,009 | 1/1989 | Yamazaki ................................ 384/100 |
| 4,817,586 | 4/1989 | Wampler .................................. 600/16 |
| 4,846,152 | 7/1989 | Wampler et al. .......................... 600/16 |
| 4,908,012 | 3/1990 | Moise et al. .............................. 600/16 |
| 4,944,722 | 7/1990 | Carriker ................................... 600/16 |
| 4,944,748 | 7/1990 | Bramm et al. ............................. 623/3 |
| 4,957,504 | 9/1990 | Chardack .................................. 623/3 |
| 4,994,078 | 2/1991 | Jarvik ......................................... 623/3 |
| 5,049,134 | 9/1991 | Golding et al. .......................... 604/151 |
| 5,055,005 | 10/1991 | Kletschka ................................ 417/356 |
| 5,507,629 | 4/1996 | Jarvik .................................... 417/423.3 |
| 5,588,812 | 12/1996 | Taylor et al. ............................ 417/356 |
| 5,707,218 | 1/1998 | Maher et al. ............................ 417/356 |

OTHER PUBLICATIONS

"In Vitro Performance of the Baylor/NASA Axial Flow Pump," Damm et al, *Artificial Organs,* 1993, vol. 17 #7, pp. 609–613.

"Development of Baylor/NASA Axial Flow Ventricular Assist Device: In Vitro Performance and Systematic Hemolysis Test Resulsts," Mizuguchi et al, *Artificial Organs,* 1994, vol. 18, pp. 32–43.

*Primary Examiner*—Timothy S. Thorpe
*Assistant Examiner*—Ehud Gartenberg
*Attorney, Agent, or Firm*—Hardie R. Barr

[57] ABSTRACT

Methods and apparatus are provided for a blood pump bearing system within a pump housing to support long-term high-speed rotation of a rotor with an impeller blade having a plurality of individual magnets disposed thereon to provide a small radial air gap between the magnets and a stator of less than 0.025 inches. The bearing system may be mounted within a flow straightener, diffuser, or other pump element to support the shaft of a pump rotor. The bearing system includes a zirconia shaft having a radiused end. The radiused end has a first radius selected to be about three times greater than the radius of the zirconia shaft. The radiused end of the zirconia shaft engages a flat sapphire endstone. Due to the relative hardness of these materials a flat is quickly produced during break-in on the zirconia radiused end of precisely the size necessary to support thrust loads whereupon wear substantially ceases. Due to the selection of the first radius, the change in shaft end-play during pump break-in is limited to a total desired end-play of less than about 0.010 inches. Radial loads are supported by an olive hole ring jewel that makes near line contact around the circumference of the shaft to support high speed rotation with little friction. The width of olive hole ring jewel is small to allow heat to conduct through to thereby prevent heat build-up in the bearing. A void defined by the bearing elements may fill with blood that then coagulates within the void. The coagulated blood is then conformed to the shape of the bearing surfaces.

9 Claims, 11 Drawing Sheets

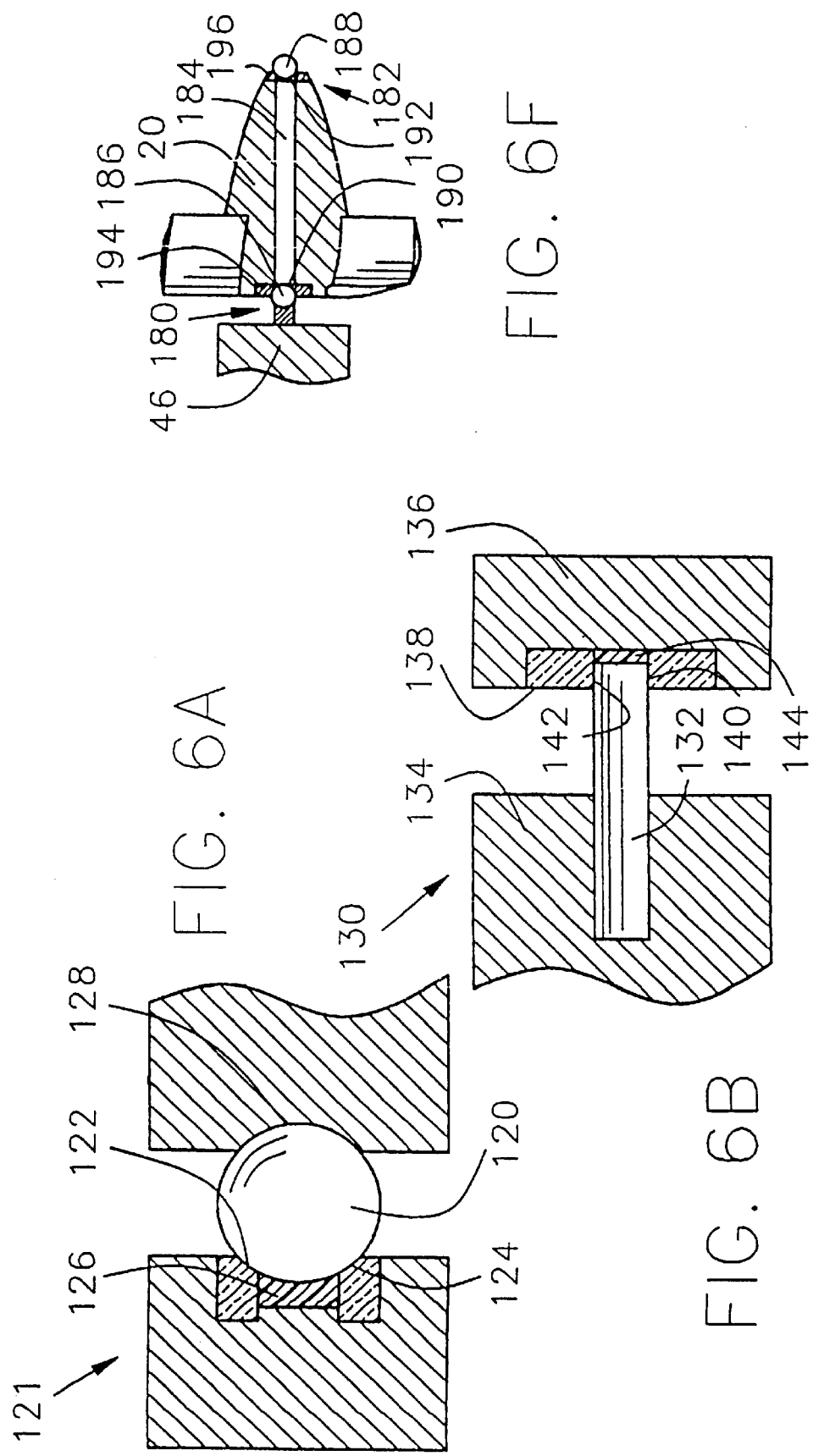

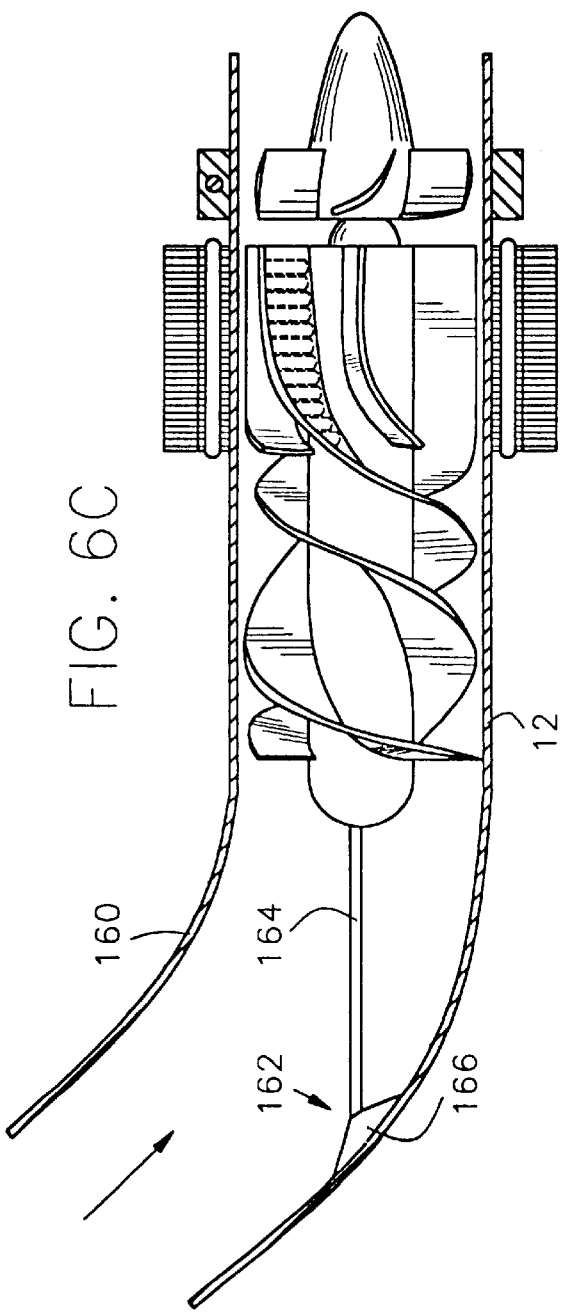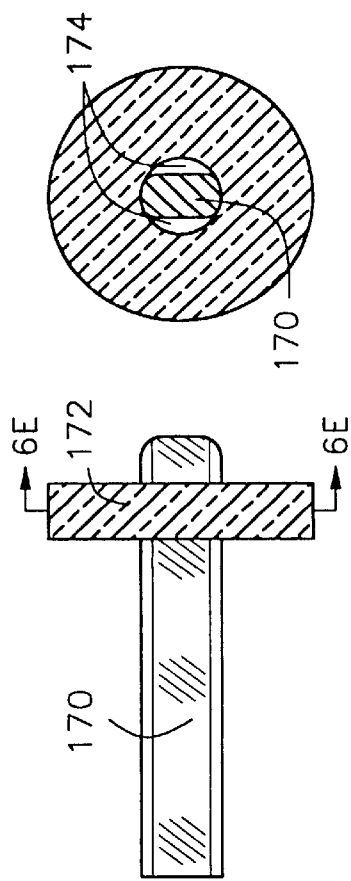

FIG. 7

TABLE OF PUMP COMPONENTS

| PARAMETER | FLOW STRAIGHTENER | INDUCER | IMPELLER | DIFFUSER |
|---|---|---|---|---|
| ENTRANCE ANGLE (DEGREES) | | | | |
| PRESENT PREFERENCE | 90 | 10 | 15 | 15 |
| PREFERRED RANGE | 80–90 | 10–20 | 10–25 | 10–25 |
| OUTLET ANGLE (DEGREES) | | | | |
| PRESENT PREFERENCE | 90 | 20 | 90 | 90 |
| PREFERRED RANGE | 80–90 | 10–25 | 80–90 | 80–90 |
| PREFERRED MIDPOINT | N/A | 35 | N/A | |
| MIDPOINT RANGE | N/A | 30–45 | N/A | |
| MAX THICKNESS (INCHES) | 0.030 | 0.035 | 0.070 | 0.040 |
| AXIAL CLEARANCE (INCHES) | | | | |
| PRESENT PREFERENCE | N/A | 0.040 | N/A | 0.025 |
| PREFERRED RANGE | N/A | 0.010–0.050 | N/A | 0.010–0.050 |
| RADIAL CLEARANCE (INCHES) | | | | |
| PRESENT PREFERENCE | 0 | 0.005 | 0.005 | 0 |
| PREFERRED RANGE | N/A | 0.003–0.015 | 0.003–0.015 | N/A |
| LENGTH (INCHES) | 0.300 | 0.400 | 0.675 | 0.300 |
| WRAP (DEGREES) | | | | |
| PRESENT PREFERENCE | N/A | 240 | N/A | N/A |
| PREFERRED RANGE | N/A | 200–300 | N/A | N/A |
| NUMBER OF BLADES | | | | |
| PRESENT PREFERENCE | 4 | 3 | 6 | 6 |
| PREFERRED RANGE | 2–4 | 2–6 | 2–6 | 5–8 |
| OVERLAP (DEGREES) | | | | |
| PRESENT PREFERENCE | N/A | 120 | N/A | N/A |
| PREFERRED RANGE | N/A | 100–200 | N/A | N/A |

FIG. 8

AXIAL FLOW PUMP TEST MATRIX

| Test variables TEST # | No 1 BLADE TIPS (IMPELLER) | No 2 RADIAL CLEARANCE | No 3 AXIAL CLEARANCE | No 4 # OF BLADES (IMPELLER) | No 5 # OF BLADES (STATOR) | No 6 IMPELLER LENGTH |
|---|---|---|---|---|---|---|
| 1 | FLAT | 0.013" | 0.025" | 6 | 5 | 0.675" |
| 2 | ROUNDED | 0.013" | 0.025" | 6 | 5 | 0.675" |
| 3 | SEE NOTE A | 0.026" | 0.025" | 6 | 5 | 0.675" |
| 4 | " | 0.039" | 0.025" | 6 | 5 | 0.675" |
| 5 | " | SEE NOTE B | 0.025" | 6 | 5 | 0.675" |
| 6 | " | " | 0.050" | 6 | 5 | 0.675" |
| 7 | " | " | 0.075" | 4 | 5 | 0.675" |
| 8 | " | " | SEE NOTE C | 2 | 5 | 0.675" |
| 9 | " | " | " | SEE NOTE D | 4 | 0.675" |
| 10 | " | " | " | " | 3 | 0.675" |
| 11 | " | " | " | " | 2 | 0.675" |
| 12 | " | " | " | " | SEE NOTE E | 0.338" |
| 13 | FLAT | 0.009" | 0.025" | 6 | 5 | 0.675" |
| 14 | FLAT | 0.005" | 0.025" | 6 | 5 | 0.675" |
| 15 | FLAT | 0.009" | 0.025" | 2 | 5 | 0.675" |
| 16 | FLAT | 0.005" | 0.025" | 2 | 5 | 0.675" |

NOTES:
A - USE OPTIMUM BLADE TIP GEOMETRY FROM TESTS 1 AND 2
B - USE OPTIMUM RADIAL CLEARANCE FROM TESTS 1 - 4
C - USE OPTIMUM STATOR ROTOR CLEARANCE FROM TESTS 1 - 6
D - USE OPTIMUM NUMBER OF IMPELLER BLADES FROM TESTS 1-8
E - USE OPTIMUM NUMBER OF STATOR BLADES FROM TESTS 1-11

Test Conditions:
- 5 Liters/Minute against 100 mmHg
- 20 minute duration
- 500 ml Bovine blood

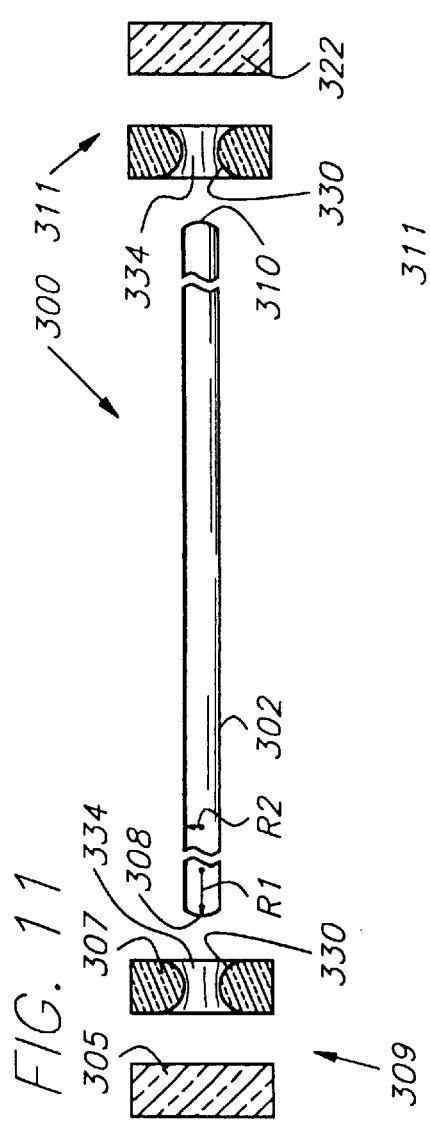
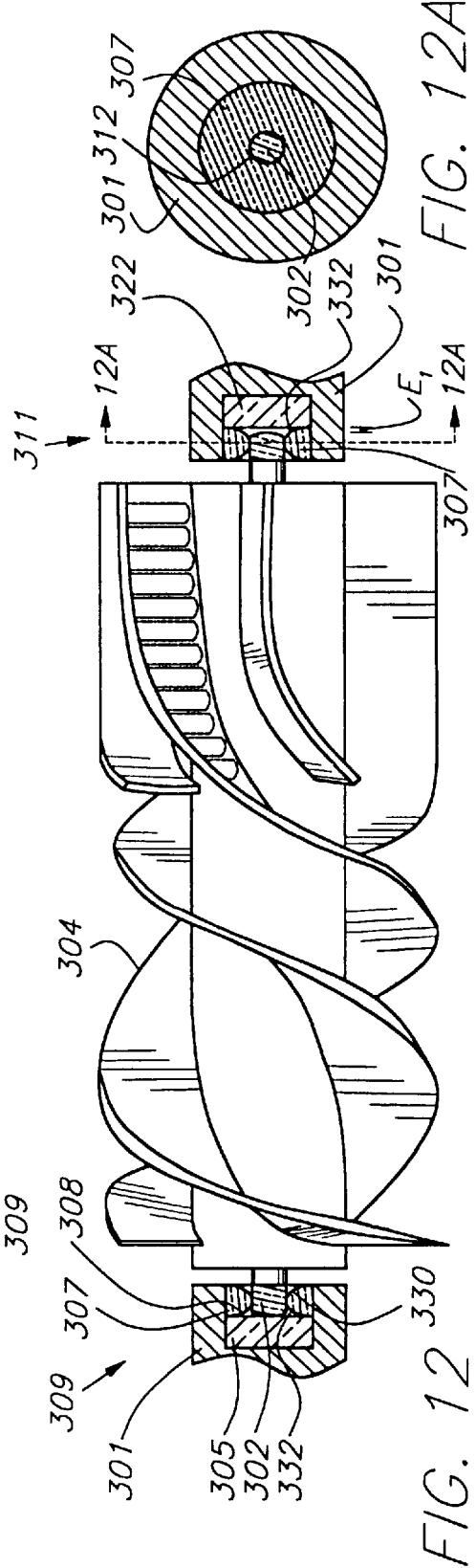
FIG. 11
FIG. 12
FIG. 12A

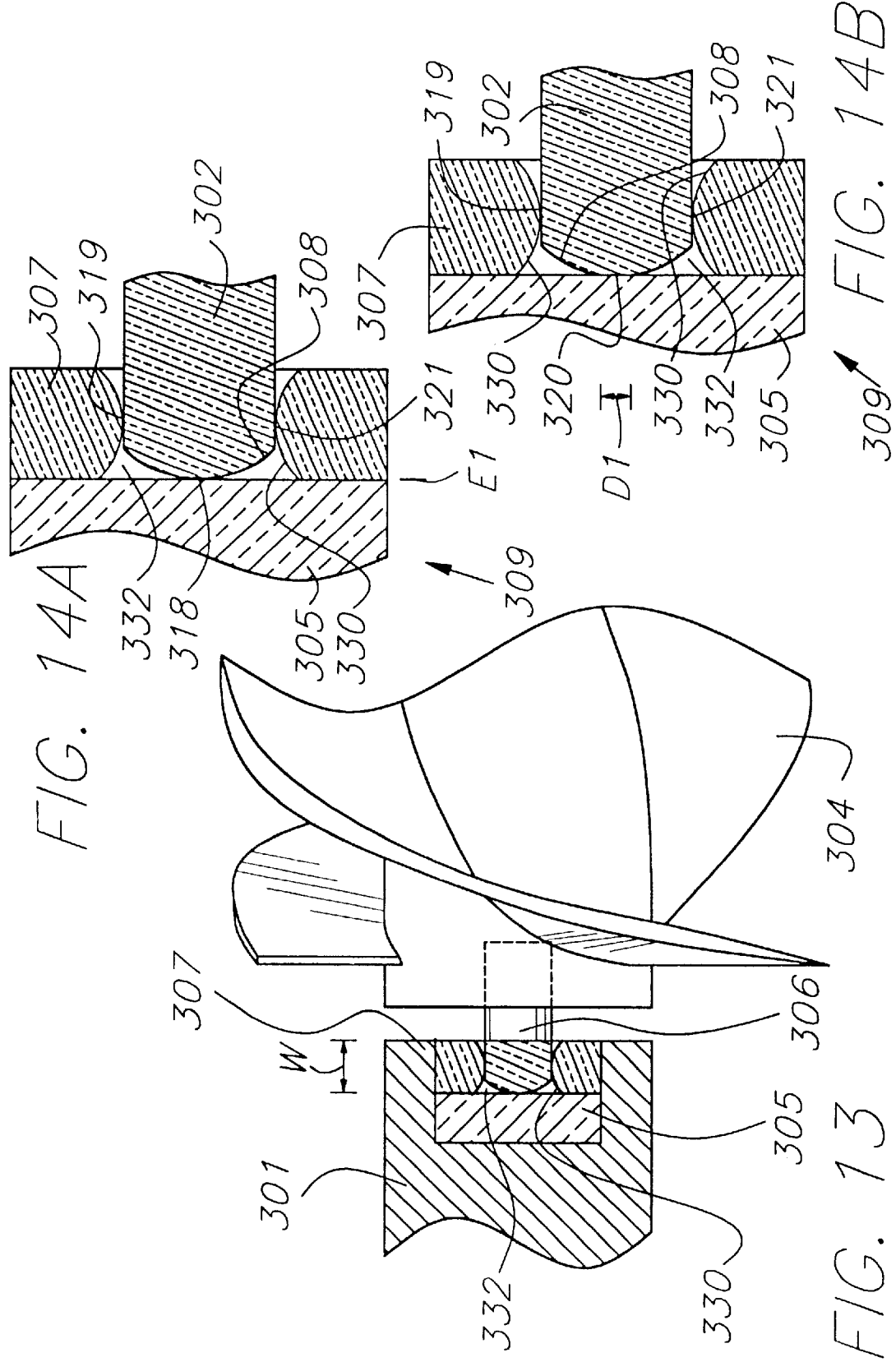

BLOOD PUMP BEARING SYSTEM

This application is a continuation-in-part of U.S. application Ser. No. 08/153,595 filed Nov. 10, 1993, U.S. Pat. No. 5,527,159 and of U.S. application Ser. No. 08/451,709 filed May 26, 1995 U.S. Pat. No. 5,678,306.

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

1. Technical Field

The present invention relates generally to rotary blood pumps. More specifically, the present invention relates to a ventricle assist device having a bearing system for supporting long-term high speed rotor rotation with minimal friction and heat build-up.

2. Background Art

Ventricle assist devices are frequently used to boost blood circulation to assist a heart which still functions but is not pumping sufficient blood for adequate circulation. The estimated need for a reliable long-term ventricle assist device (VAD) is presently projected at between 50,000 and 100,000 patients per year in the United States alone.

At the present time, rotary blood pumps are often the preferred type of pump for use as a ventricle assist device as compared to other more complex types of pumps which may use pistons, rollers, diaphragms, compliance chambers, and so forth. This is at least partially because rotary pumps may be manufactured in larger numbers at a relatively lower cost and are typically less complex than other types of pumps. The more complex pumps, on the other hand, may cost up to $50,000 per unit. Furthermore, availability of large numbers of complex pumps, as is required by the sizeable population that could benefit from such pumps, is limited by high manufacturing, operating, and maintenance costs. Therefore, rotary blood pumps are increasingly used not only for ventricular assist applications, but also for cardiopulmonary bypass procedures and percutaneous cardiopulmonary support applications in emergency cases.

Clinical uses of rotary pumps are normally limited to a few days owing to shortcomings of the devices. A non-comprehensive list of such problems or shortcomings would include the following: (1) blood damage which may occur when blood comes into contact with rotor bearings due to bearing heat or being forced through small clearances, (2) the need for bearing purge systems which may require percutaneous (through the skin) saline solution pump systems, (3) bearing seizure resulting from the considerable thrust and torque loads, or from dried blood sticking on the bearing surfaces, (4) problems of blood damage (hemolysis) and blood clotting (thrombosis) caused by relative rotational movement of the components of the pump, (5) pump and control size and shape limitations necessary for implantation or convenient mobility, (6) weight limitations for implantation to avoid tearing of implant grafts due to inertia of sudden movement, (7) difficulty in coordinating and optimizing the many pump design parameters which may affect hemolysis, (8) high power consumption that requires a larger power supply, (9) motor inefficiency caused by a large air gap between motor windings and drive magnets, (10) heat flow from the device to the body, (11) complex Hall Effect sensors/electronics for rotary control, (12) the substantial desire for minimizing percutaneous (through the skin) insertions including support lines and tubes, (13) large pump and related hose internal volume which may cause an initial shock when filled with saline solution while starting the pump, and other problems.

Existing bearing systems for externally used rotary blood pumps may have small rolling element bearings such as ball bearings. Rolling element bearings require a shaft seal to prevent blood entering the bearing voids between the rolling elements. If blood enters the bearing voids, it coagulates and may cause bearing seizure by interfering with the rolling elements. Shaft seals complicate pump design, decrease pump reliability, and reduce pump life.

Some implantable blood pumps utilize pivot bearings. Pivot bearings can operate immersed in blood without a blood seal. However, to maintain the precise rotation required in blood pumps to minimize red blood cell damage, such pivot bearings utilize complicated shaft pre-load mechanisms to eliminate shaft end-play. Shaft pre-load mechanisms are prone to seizure by coagulated blood. They also increase bearing wear.

Other blood pump bearing systems utilize journal bearings flushed with fluids such as saline solution or blood. Journal bearings have minimal wear, but require a separate thrust bearing that complicates pump design. Journal bearings require fluid pressure to support the loads. If the pump utilizes saline solution rather than blood as the bearing fluid, then pump design is significantly complicated by the need for a separate reservoir, flow lines, and the like. If the pump utilizes blood as bearing fluid, then potential pump seizure caused by coagulated blood is a serious concern. In addition, blood flow through a journal bearing is exposed to a high shear environment. The high shear environment may damage the blood or generate micro-clots that are washed into the patients blood stream. Finally, journal bearings of the size used in blood pumps require very precise alignment that increase manufacturing complexity, and increase costs.

Although a significant amount of effort has been applied to solving the problems associated with rotary pumps, there is still a great demand for a safe, reliable, and durable blood pump that may be used for longer term applications.

The following patents describe attempts made to solve problems associated with rotary blood pumps including ventricle assist devices.

U.S. Pat. No. 4,625,712 to R. K. Wampler discloses a full-flow cardiac assist device for cardiogenic shock patients which may be inserted into the heart through the femoral artery and driven via flexible cable from an external power source. A catheter attached to the pump supplies the pump bearings with a blood-compatible purge fluid to prevent thrombus formation and introduction of blood elements between rotating and stationary elements. Due to the very small diameter of the pump, rotational speeds on the order of 10,000 to 20,000 rpm are used to produce a blood flow on the order of about four liters per minute.

U.S. Pat. No. 4,957,504 to W. M. Chardack discloses an implantable blood pump for providing either continuous or pulsatile blood flow to the heart. The pump includes a stator having a cylindrical opening, an annular array of electromagnets disposed in a circle about the stator concentric with the cylindrical opening, a bearing carried by the stator and extending across the cylindrical opening, and a rotor supported by the bearing. The rotor is in the form of an Archimedes screw and has a permanent magnet in its periphery which lies in the same plane as the circular array of electromagnets and is driven in stepper motor fashion.

U.S. Pat. No. 4,944,722 to J. W. Carriker discloses a percutaneously insertable intravascular axial flow blood pump with a rotor extension and drive cable fitting so designed that the thrust bearing surfaces of the purge seal and cable fitting can be pre-loaded.

U.S. Pat. No. 4,817,586 to R. K. Wampler discloses an intravascular flow blood pump with reduced diameter having blood exit apertures in the cylindrical outside wall of the pump housing between the rotor blades and the rotor journal bearing.

U.S. Pat. No. 4,908,012 to Moise et al. discloses an implantable ventricular assist system having a high-speed axial flow blood pump. The pump includes a blood tube in which the pump rotor and stator are coaxially contained, and a motor stator surrounding the blood duct. A permanent magnet motor rotor is integral with the pump rotor. Purge fluid for the hydrodynamic bearings of the device and power for the motor are preferably percutaneously introduced from extra-corporeal sources worn by the patient.

U.S. Pat. No. 4,779,614 to J. C. Moise discloses an implantable axial flow blood pump which includes a magnetically suspended rotor of relative small diameter disposed without bearings in a cylindrical blood conduit. Neodymium-boron-iron rotor magnets allow a substantial gap between the static motor armature and the rotor. Magnetically permeable strips in opposite ends of the pump stator blades transmit to Hall sensors variations in an annular magnetic field surrounding the rotor adjacent the ends of the pump stator blades.

U.S. Pat. No. 5,049,134 to Golding et al. discloses a seal free centrifugal impeller supported in a pump housing by fluid bearings through which a blood flow passageway is provided.

U.S. Pat. No. 4,382,199 to M. S. Isacson discloses a hydrodynamic bearing system for use with a left ventricle assist device. The bearings are formed by the fluid in the gap between the rotor and the stator.

U.S. Pat. No. 4,135,253 to Reich et al. discloses a centrifugal blood pump provided with a magnetic drive system which permits a synchronous magnetic coupling with a separate power unit disposed immediately adjacent the pump housing but outside of the skin surface. The pump has a single moving part which includes the combination of an impeller connected to a magnetic drive rotor. The magnetic drive system floats on a fluid surface of saline solution.

U.S. Pat. No. 4,507,048 to J. Belenger discloses a centrifugal blood pump with a bell shaped housing having a suction inlet at the apex and a tangential outlet adjacent the base. A conical rotator is driven by spaced permanent magnets embedded in the base of the rotator and an externally generated rotating magnetic field.

U.S. Pat. No. 4,688,998 to Olsen et al. discloses a pump with a magnetically suspended and magnetically rotated impeller. The impeller may be configured for axial flow with a hollow, cylindrical-type impeller with impeller vanes on the internal surface thereof. The impeller includes a plurality of internally embedded, permanent magnets that cooperate with electromagnets for drive and position control of the impeller.

U.S. Pat. No. 4,763,032 to Bramm et al. discloses a magnetic rotor bearing for suspending a rotor for an axial or radial-centrifugal blood pump in a contact-free manner, and comprising a permanent and electromagnetic arrangement.

U.S. Pat. No. 4,846,152 to Wampler et al. discloses a miniature high-speed intravascular blood pump with two rows of rotor blades and a single row of stator blades within a tubular housing. The rotor's first row has no provision for a variable pitch blade but produces a mixed centrifugal and axial flow by increasing hub diameter. The rotor's second row, axially spaced and having an axial distance between the first row, produces a purely axial flow. The stator blades are reverse twisted to straighten and slow the blood flow.

U.S. Pat. No. 4,944,748 to Bramm et al. discloses an impeller in a blood pump supported by permanent magnets on the impeller and pump housing and stabilized by an electromagnet on the housing. The impeller is rotated magnetically and stator coils in the housing are supplied with electric currents having a frequency and amplitude adjusted in relation to blood pressure at the pump inlet U.S. Pat. No. 4,994,078 to R. K. Jarvik discloses an electrically powered rotary hydrodynamic pump having motor windings and laminations disposed radially about an annular blood channel and having a motor rotor disposed therein such that an annular blood channel passes through the gap between the motor rotor and the windings.

U.S. Pat. No. 5,055,005 to Kletschka discloses a fluid pump with an electromagnetically driven rotary impeller levitated by localized opposed fluid forces.

In spite of the effort evidenced by the above patents, there remains the need for an improved rotary pump for use as a ventricle assist device that is reliable, compact, requires limited percutaneous insertions, and produces fewer blood damage problems such as hemolysis and thrombosis. A bearing system for an improved rotary pump should reliably and precisely support the rotor for long-term, maintenance free, low friction operation without the need for bearing seals and lubrication. Those skilled in the art will appreciate the present invention which addresses these and other problems.

STATEMENT OF THE INVENTION

The present invention provides a blood pump bearing system for precisely supporting high-speed rotation of a rotor within a housing through which blood is pumped. The bearing system includes a shaft to support the rotor. The shaft has a circumference defined by a first radius. The shaft terminates at a shaft end that has a radiused surface defined by a second radius. The second radius is greater than the first radius and preferably is about three times greater. A shaft end bearing surface mounted to the housing operates to contact the shaft end for supporting axial loads on the shaft. The shaft end bearing surface and the shaft end form a pivot bearing. A shaft circumferential bearing mounted to the housing has an aperture therethrough for receiving the circumference of the shaft. The shaft circumferential bearing is operable to support radial loads on the shaft. The shaft circumferential bearing prevents radial but not rotational movement between the shaft end bearing surface and the shaft end that comprise the pivot bearing.

The shaft end bearing surface is preferably comprised of a first material that is harder than a second material that forms the shaft end. For this reason, wear occurs on the shaft end to quickly produce a flat surface on the radiused surface of the shaft end. After the flat surface is large enough to support axial thrust loads, wear substantially ceases to occur. At that time, the flat surface preferably has a diameter of less than about 0.025 inches. The second radius is selected such that the change of shaft axial end-play due to creation of the flat surface is preferably less than about 0.005 inches. The total shaft axial end-play after break-in is preferably less than about 0.010 inches.

The shaft end bearing surface includes a flat planar surface that contacts the radiused surface of the shaft end prior to break-in of the bearing and that contacts the created flat surface after bearing break-in.

The shaft circumferential bearing further comprises a curved inner surface that defines the aperture for receiving the shaft. This curved inner surface makes line contact along the circumference of the shaft. This line contact is very small to thereby minimize friction and heat build-up in the blood pump bearing system as the rotor rotates. The locus of line contact has a width of less than about 0.010 inches. The shaft circumferential bearing may comprise a commercially available jewel typically known as an olive hole ring jewel by those skilled in the art. The jewel bearing preferably has a substantially doughnut-shaped or toroidal curved inner surface portion that defines the aperture. The olive hole ring jewel preferably has a width as measured parallel to an axis of the shaft that is as narrow as possible to allow for heat transfer through the bearing. Preferably the width is less than about 0.035 inches and tailor bearing jewels may be obtained with significantly smaller widths. The radial clearance between the shaft circumference bearing and the circumference of the shaft is about 0.0001–0.0002 inches.

A void is formed between the shaft end and the shaft end bearing into which blood may leak between the circumference of the shaft and the shaft circumference bearing. This blood coagulates and becomes trapped in the void. Additional blood is then prevented from flowing into the void.

The blood pump bearing system shaft may be integral to the rotor section, it may be a single separate shaft mounted at both ends, or it may comprise two end sections.

The present invention also provides a method and apparatus for a rotary blood pump electromagnetic drive and includes a pump housing defining a blood flow path therethrough. A first stator having a first stator field winding is used to produce a first stator magnetic field. A first rotor is mounted within the pump housing for rotation in response to the first stator magnetic field. The first rotor carries a blade thereon to propel blood through the pump housing along the blood flow path. At least one magnet is secured to the first rotor and produces a first rotor magnetic field that passes through the first stator field winding during rotation of the first rotor to thereby induce a back emf within the first stator field winding. Back emf sensor circuitry connecting to the first stator field winding senses back emf produced during the rotation of the first rotor within the pump housing. In one embodiment of the present invention, at least one magnet is implanted in each of a plurality of impeller blades to produce rotational movement of the rotor.

The rotary pump also includes, in a preferred embodiment, an inducer portion of the rotor having a plurality of inducer blades equidistantly disposed about a circumference of the rotor with each inducer blade having a variable pitch along its axial length. An interconnection blade portion connects at least one of the inducer blades to at least one impeller blade to form a continuous blade extending through the inducer and impeller portions of the rotor.

An object of the present invention is to provide an improved rotary blood pump.

Another object of the present invention is to provide axial and radial support of a high-speed spinning impeller used to increase or sustain blood flow for a cardiac patient.

A further object is to provide an improved control circuit for controlling a rotor within the pump in response to a back emf produced in stator windings.

Another object is to provide an improved rotor bearing for which cross-linked blood forms a bearing surface and blood seal.

Yet another object of the present invention is to provide a method for optimizing pump parameters to reduce blood hemolysis to minimum.

Yet another object of the present invention is to provide a highly reliable, low friction bearing to support the rotor for high speed operation while limiting bearing temperature without the need for bearing lubrication.

A feature of the present invention is a reduced air gap between permanent magnets on the rotor and the stator winding.

Another feature of the present invention is an impeller having a variable pitch blade.

Another feature of the present invention is a back emf integrated circuit for controlling rotor operation.

Yet another feature of the present invention is a rotor shaft having a radiused end with a radius greater than the radius of the shaft circumference and preferably about three times greater.

Yet another feature of the present invention is an olive hole ring jewel to support the rotor shaft along a low friction, low heat, near line contact surface around the circumference of the rotor shaft.

Yet another feature of the present invention is a near point contact between the radiused end of the rotor shaft and a flat endstone produced when the radiused end is worn during break-in of the pump to form a small flat of the precise size necessary to support thrust loads after which wear substantially ceases thereafter.

An advantage of the present invention is improved rotor control.

Another advantage of the present invention is quantifiably reduced damage to blood.

Yet another advantage of the present invention is an elimination of the need for a bearing purge system requiring saline carrying tubes penetrating through the skin.

Yet another advantage of the present invention is the avoidance of the need for bearing seals, blood forced through close tolerance moving components, excessive bearing heat, corrosive bearing components, pre-load mechanisms, and bearing lubrication.

Other objects, features and intended advantages of the present invention will be readily apparent by the references to the following detailed description in connection with the accompanying drawings and claims.

BRIEF DESCRIPTION OF THE DRAWINGS

FIG. 6A is an elevational view, partially in section, of a ball-socket rotor bearing having a bearing chamber filled with bio-compatible material;

FIG. 6B is an elevational view, partially in section, of a shaft journal rotor bearing having a bearing chamber filled with bio-compatible material;

FIG. 6C is an elevational view, partially in section, having a rotor bearing washed from increased blood flow caused by bend in the pump housing;

FIG. 6D is an elevational view, partially in section, showing a cross-section of a rotor bearing shaft having blood flow passages along the shaft periphery;

FIG. 6E is a cross-sectional view along line 6E—6E;

FIG. 6F is an elevational view, partially in section, of a rotor bearing for supporting the rotor in cantilevered fashion;

FIG. 7 is a chart showing optimum pump parameter components determined from methods of optimizing pump parameters to minimize hemolysis;

FIG. 8 shows the test matrix of the present invention for optimizing pump parameters to minimize hemolysis while maximizing pump efficiency;

FIG. 11 is an elevational view, partially in section, of components of a bearing system in accord with the present invention;

FIG. 12 is an elevational view, partially in section, of components of the invention supporting a blood pump rotor in accord with the present invention;

FIG. 12A is a cross-sectional view along the line 12A—12A;

FIG. 13 is an enlarged elevational view, partially in section, of one end of a rotor bearing system in accord with the present invention;

FIG. 14A is an enlarged elevational view, in section, showing point contact at end of the radiused shaft prior to pump break-in; and FIG. 14B is an enlarged elevational view, in section, showing a flat worn on the radiused shaft after pump break-in in accord with the present invention.

While the invention will be described in connection with the presently preferred embodiments, it will be understood that it is not intended to limit the invention to these embodiments. On the contrary, it is intended to cover all alternatives, modifications, and equivalents as may be included in the spirit of the invention.

DESCRIPTION OF THE PREFERRED EMBODIMENTS

The present invention describes a rotary blood pump which has an improved rotor control system. The rotary pump has pump blade geometry optimized by a method of the present invention to provide high pump efficiency while minimizing hemolysis and thrombus (hemolysis is defined quantitatively hereinafter). The pump requires less than 10 watts of power to pump 5 liters/minute against a pressure head of 100 mm Hg. A preferred embodiment of the pump weighs 53 grams and has a length of 75 mm and a diameter of 25 mm. An index of hemolysis of from 0.003 to 0.005 g/100 liters pumped has been achieved, although using the method of this invention, further reductions are possible. For reference, a standard roller pump has an index of hemolysis of 0.06 g/100 liters. Published articles concerning aspects of the present invention are hereby incorporated by reference and include the following: (1) "In Vitro Performance of the Baylor/NASA Axial Flow Pump", *Artificial Organs,* 1993 Volume 17, number 7, page 609–613; (2) "Development of Baylor/NASA axial flow VAD, *Artificial Organs,* 1993, Volume 17, page 469.

Figure 1:
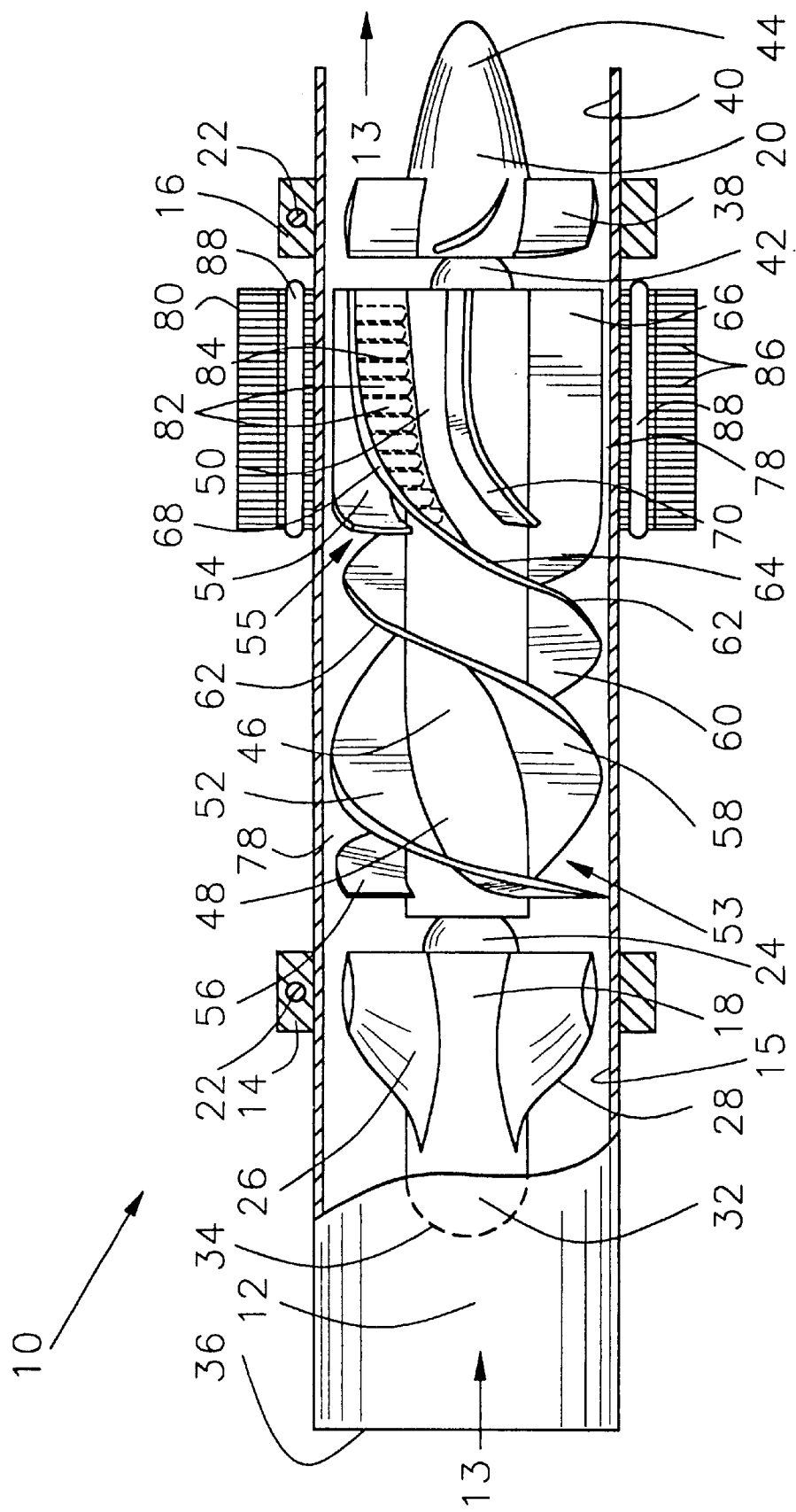
FIG. 1 is an elevational view, partially in section, of a rotary blood pump in accord with the present invention.

Referring now to the drawings, and more particularly to FIG. 1, there is a shown a rotary blood pump 10 in accord with the present invention. Blood pump 10 includes a preferably metallic tubular pump housing 12 which is, in a preferred embodiment, a straight-sided cylinder. Pump housing 12 has a smooth inner bore wall 15 to minimize thrombus formation. Pump housing 12 defines an axial blood flow path 13 therethrough in the direction indicated by blood flow arrows shown in FIG. 1.

Front and rear clamps 14 and 16, respectively, are used to secure flow straightener 18 and diffuser 20 within pump housing 12. Pump housing 12 is sufficiently thin-walled so that the tightening of clamps 14 and 16 with clamp screws 22 locally deforms pump housing 12 about flow straightener 18 and diffuser 20 to affix these components in position. The clamps provide a very convenient means of securing the rotor assembly. Alternatively, other means for securing these components could be used such as spot welding, fasteners, interference fit, and so forth.

Flow straightener 18 serves two basic functions (1) it straightens blood flow to reduce hemolysis while improving pump efficiency (2) it provides a support structure for front ball-socket bearing assembly 24 as discussed hereinafter. By straightening the flow of blood as it initially flows into the entrance 36 of pump 10, hydraulic efficiency is increased. Straightening the blood flow reduces turbulence to increase the pump pressure. FIG. 7 lists optimal values and permissible pump parameter ranges of values for flow straightener 18 and other pump components.

Figure 3:
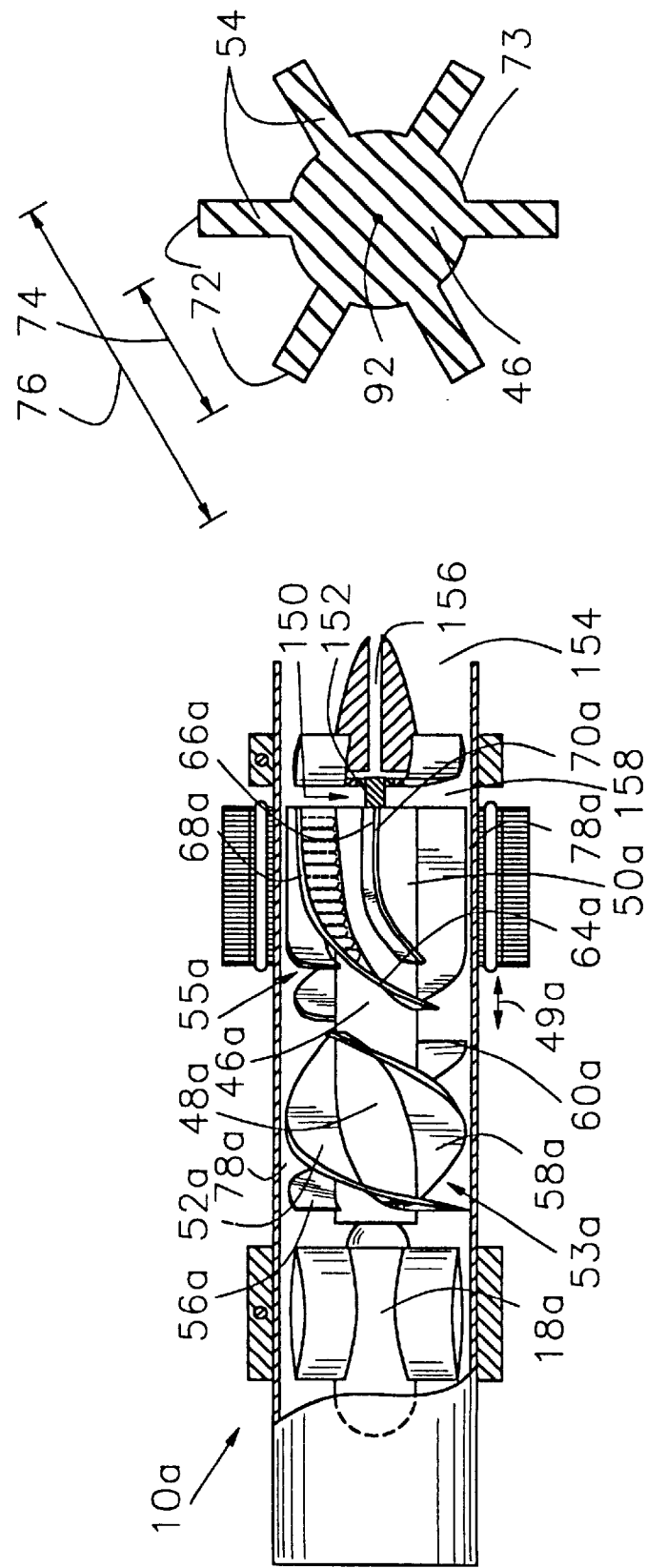
FIG. 3 is an elevational view, partially in section, of an alternative embodiment rotary blood pump having distinct impeller and inducer blades.

Flow straightener 18 preferably has four fixed blades 26 but may have from two to four blades. Too many blades impede blood flow while too few blades reduce pump efficiency. For purposes of lowering thrombosis, the front edge 28 of blades 26 is sloped from inner housing wall 15 to flow straightener hub 32 so that blood trauma by contact with blades 26 is minimized. Also to reduce blood trauma, flow straightener hub 32 is cylindrical with a round leading surface 34. Surface 34 may also be hyperbolical or generally bullet-shaped for this purpose. An alternative embodiment flow straightener 18a is shown in FIG. 3 and does not have the sloping front edge blades.

The preferred angle of attack of blades 26 is 90° i.e. the blades would intersect a plane transverse to cylindrical housing 12 at an angle of 90°. This reference for the angle of attack or pitch of the blades will be used throughout this specification.

Flow straightener 18 is preferably metallic but may also be formed of plastic. If formed of plastic and secured in place by clamp 14, it is necessary to reinforce flow straightener 18 with, for instance, metallic supports to prevent plastic creep deformation. The plastic creep deformation phenomena might otherwise eventually cause flow straightener 18 to come loose from clamp 14. Reinforcement is also necessary with respect to other clamped plastic pump components.

Diffuser 20 also has two basic purposes: (1) it de-accelerates and redirects the outflow at blood flow path exit 40 axially to boost pump performance and (2) it serves as a support structure for rear rotor bearing 42. Diffuser 20 preferably has from 5 to 8 fixed blades 38 with 6 blades being the presently preferred optimum number. Blades 38 are fixably engaged with pump housing 12 after rear clamp 16 is tightened as by screw 22.

To perform the function of de-acceleration and axial redirection of blood flow, each diffuser blade 38 has an entrance angle of from about 10° to 25° for slowing the blood down and an outlet angle of from about 80° to 90° for redirecting blood flow in an axial direction. Presently preferred blade geometry is listed in FIG. 7 and includes an entrance angle of 15° and an outlet angle of 90°. Tail cone 44 of diffuser 20 is hyperbolical or generally bullet shaped to reduce turbulence or wake of blood flow from pump 10 so as to minimize blood damage from such turbulence. Somewhat surprisingly, it was found that increasing the number of fixed blades tends to decrease hemolysis.

Rotor 46 is supported for rotary movement with pump housing 12 by front and rear bearings 24 and 42, respectively. Rotor 46 is divided into two portions along its axis based on the type and function of the blades disposed thereon. Inducer portion 48 of rotor 46 is disposed in the front part, with respect to blood flow direction, of rotor 46 closest to pump inlet 36. Impeller portion 50 is disposed in the rear part of rotor 46 closest to pump outlet 40. It has been found that including an inducer portion in an axial flow pump, along with an impeller portion, significantly reduces hemolysis.

FIG. 3 shows an alternative embodiment pump 10a of the present invention which provides for two distinct sets of axially spaced blades which more clearly distinguish the inducer portion of the rotor from the impeller portion of the rotor. Corresponding components of pump 10 and 10a are given the same number, with the difference of an "a" suffix to distinguish the components for comparison purposes as necessary. A reference to one number is therefore a reference to its corresponding number in this specification, unless otherwise stated. Where components are substantially different between the two pump versions, completely new numbers are assigned. In pump 10a, inducer portion 48a is separated from impeller portion 50a of rotor 46a by gap 49a which is preferably less than 0.10 inches. Inducer blade 52a may be tapered (not shown) at forward end 56a so that blade 52a has a smaller radial length at forward end 56a, perhaps even blending into hub 73. However, using the method of the present invention, it has been found that a continuous blade pump has even more reduced levels of hemolysis than the non-continuous blade pump 10a. Thus, pump 10 shown in FIG. 1 is the presently preferred embodiment.

Figure 9:
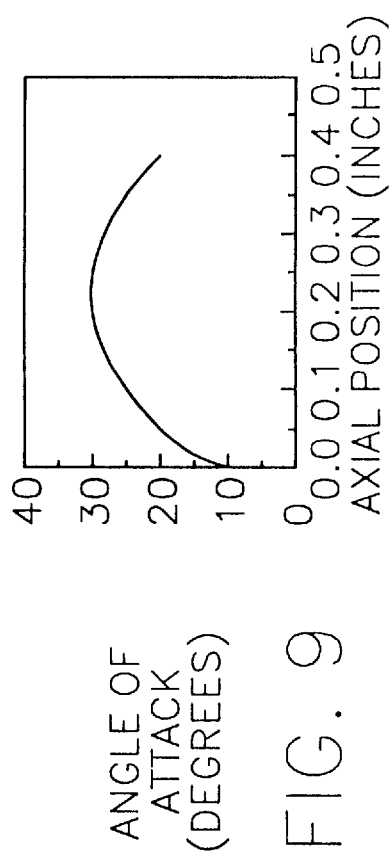
FIG. 9 is a graph showing change in inducer blade pitch along the axial length of the inducer.

Inducer blades 52 on inducer 53 have a variable pitch along their axial length. FIG. 9 shows an inducer blade angle profile that plots angle of attack in degrees versus axial position on inducer 53 in inches. It was found that the inducer portion 48 reduced hemolysis by approximately 45% from a pump design without the inducer. Hydraulic efficiency was also increased as the rotation speed required to pump 5 liters/min of blood at 100 mm Hg. dropped from 12,600 rpm to 10,800. The inducer blades pre-rotate the blood before it enters the main pumping blades (i.e. impeller blades 54) to reduce hemolysis.

Inducer blades 52 also achieve a pumping action that effectively produces a two-stage, increased efficiency pump. Optimum inducer blade geometry for minimal hemolysis and maximum pump efficiency is listed for specific parts of inducer blade 52 in the chart of FIG. 7. Thus, the entrance angle of leading end 56 of inducer blade 52 is preferably 10° but has a preferred range from about 10° to 20°. The shallow entrance angle effectively engages the blood for movement but does not damage it. The pitch of inducer blade 52 continues to change along its axial length and preferably is about 30° at midpoint 58 of the blade. The tailing end 60 of inducer blade 52 preferably has an outlet angle of 20°. This variable pitch is described in FIG. 9 which shows how pitch varies versus axial length of inducer 53. As well, it is desired that inducer blades have a wrap of preferably 240° around rotor 46. The presently preferred overlap of each blade over other blades is 120° or a 50% overlap. The chart of FIG. 7 provides a complete listing of relevant pump parameter values including preferred ranges of operation. Outside of these ranges, pump efficiency drops and/or blood damage is more likely to occur.

Pump 10 includes an interconnecting blade portion 62 which is not included in pump 10a. Although the two-stage pump 10a produces significantly reduced hemolysis and efficient pump operation as compared to a single stage pump, it has been discovered that by interconnecting inducer blades 52 with impeller blades 54 with interconnecting blade portion 62, hemolysis may be reduced to even lower levels while maintaining efficient pump operation.

Impeller blades 54 on impeller 55 have an entrance angle in leading end region 64 of preferably 20°. This may be seen more clearly in FIG. 3 which has no interconnecting blade portion 62. The entrance angle preferably smoothly tapers to an optimum preferred outlet angle of 90° at blade tailing end region 66. The optimum ranges of operation for the entrance and outlet angles is given in FIG. 7.

Impeller blades 54 include axially longer impeller blades such as longer blade 68 and axially shorter impeller blades such as shorter blade 70. The alternate long and short blade arrangement on impeller 55 accommodates multiple magnetic poles for electric motor operation as discussed hereinafter, and still maintains adequate flow area through impeller 55. Presently, the preferred number of impeller blades is six, but a range from two to six blades provides a range of permissible pump efficiency. If impeller 55 included six axially longer blades, such as longer blade 68, flow area through impeller portion 50 would be restricted to such an extent that the blades actually begin to block the flow they are intended to produce.

Using the method of this invention, it was unexpectedly discovered that hemolysis does not necessarily increase with the number of blades, as anticipated. The alternating long-short blade arrangement of the six bladed impeller of the present invention does not cause hemolysis any more significantly than a two-bladed impeller. In some cases, an impeller with four long blades may cause more hemolysis than either a two or six bladed impeller. It is possible that the degree of hemolysis depends more on the number of long blades rather than the total number of blades.

Figure 4:
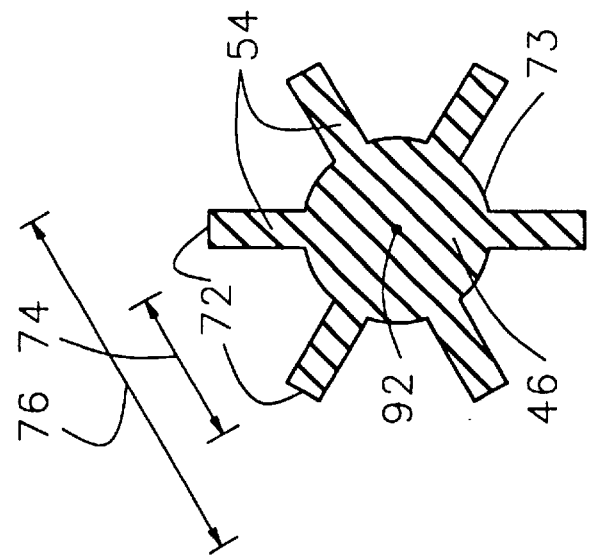
FIG. 4 is an elevational view, in section, of a portion of an impeller showing non-radiused blade tips.

FIG. 4 shows a portion of impeller 55 in cross-section to illustrate substantially flat, non-radiused blade tips 72. It has been unexpectedly found, using the method of this invention, that flat or substantially flat, non-radiused blade tips have substantially the same pump response but do not produce significantly different results from rounded or radiused blade tips with respect to hemolysis. It was anticipated that flat blade tips would produce higher hemolysis. Because flat blade tips are less expensive to manufacture in conjunction with magnets to be used in the blades as discussed hereinafter, flat blade tips comprise the presently preferred embodiment. Further test results are discussed in greater detail in the previously noted articles incorporated herein by reference.

FIG. 4 also illustrates a preferred rotor hub 73 with outside diameter 74 compared to overall outside diameter 76 of inducer 53 and/or impeller 55. The preferred ratio is 0.48 although a range of 0.45 to 0.55 permits excellent pump operation. If the hub is smaller than permitted by this range, blood becomes excessively swirled and may tend to recirculate within pump 10 in the wrong flow direction to possibly damage the blood as well as reduce pump efficiency. If the hub is too large so as to be outside of this range, the hub tends to block flow through pump 10.

The radial clearance 78 between inducer 53 and/or impeller 55 with respect to pump housing 12 inner wall 15 is preferably in the range of about 0.003 inches to 0.015 inches. Using a test matrix as per the method of this invention, it was unexpectedly discovered that smaller radial clearances lowered hemolysis. It was expected that smaller clearances would produce greater blood damage due to higher sheer stresses on the blood. The presently preferred radial clearance 78 is 0.005 inches. Axial clearances between components such as flow straightener 18, rotor 46, and diffuser 20 are shown in FIG. 7. Axial clearances should be within the ranges shown to improve pump efficiency and to reduce hemolysis.

In order to reduce air gap between stator 80 and magnets 82, the magnets are preferably sealingly mounted within impeller blades 54. Reducing the air gap between stator 80 and magnets 82 increases motor efficiency, because magnetic flux is not as diffused as occurs in motor designs with large air gaps. The preferred radial spacing or air gap between magnets 82 and stator 80 is from 0.01 inches to 0.025 inches. Magnets 82 are preferably rare earth magnets because of the higher magnetic flux produced by such magnets. Each magnet 82 is encapsulated into an individual pocket 84 to eliminate corrosion. Because magnets are individualized, motor torque and rotor weight can be easily adjusted in the manufacturing stage to provide motors that are tailored to the type of pump performance necessary without producing excessive pump weight.

Field winding 88 generates a magnetic field to rotate rotor 46. Stator 80 is comprised of individual stator laminations 86 to eliminate eddy currents that generate heat and reduce efficiency. Heat flow from pump 10 is directed both into the blood stream and into the tissues surrounding pump 10. In this way, the blood is not heated in a manner that may damage the blood and, as well, the surrounding tissues do not have to absorb all the heat. Heat conductive flow paths using thermally conductive material, such as the metal of the stator or thermally conductive gel, may be used to provide approximately the desired ratio of heat flow to tissues compared to the heat flow to the blood.

Figure 2A:
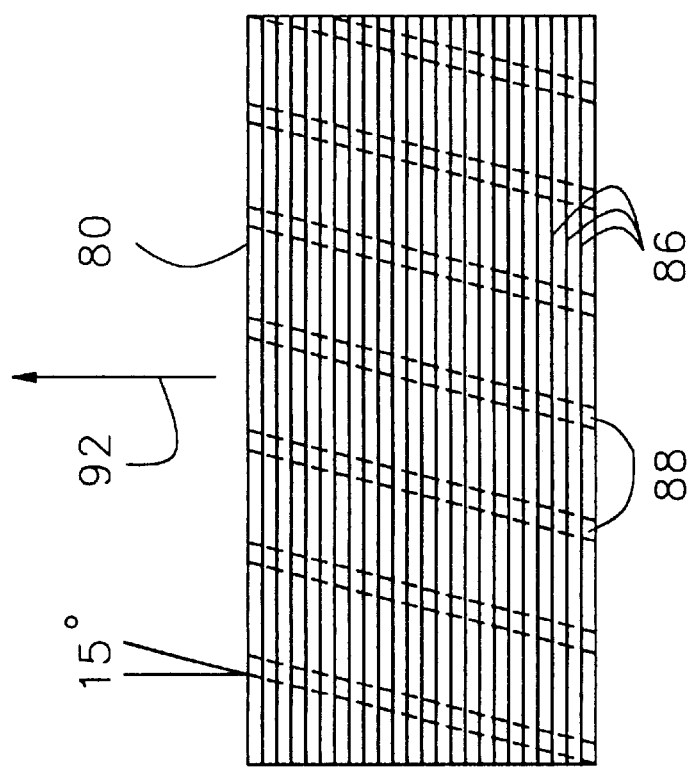
FIG. 2A is an elevational view indicating the skewed path of stator field windings through the stator.
Figure 2:
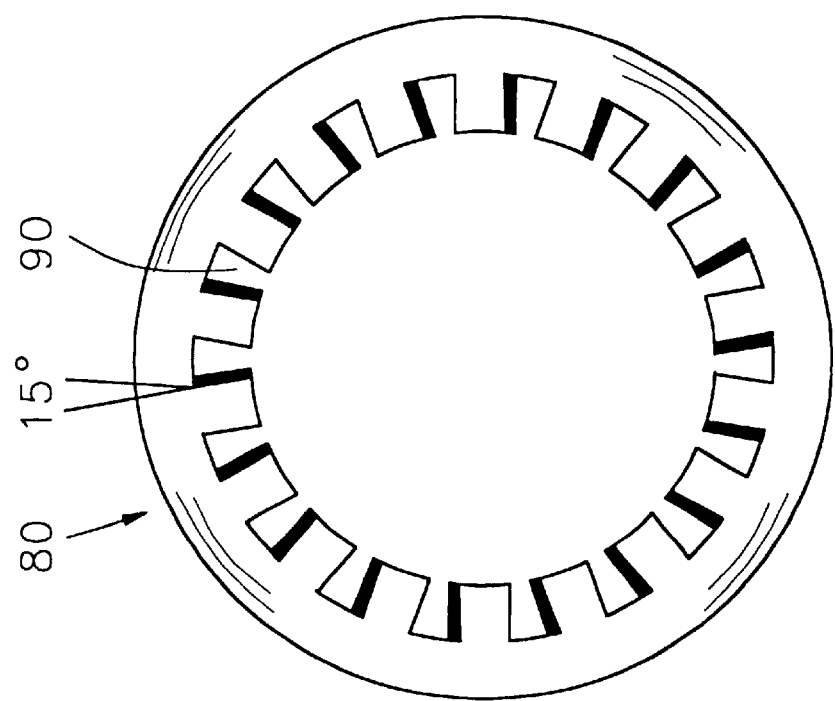
FIG. 2 is an elevational view of a stator showing stator laminations stacked together to form a skewed stator.

As illustrated in FIG. 2, stator 80, comprised of individual laminations 86, is stacked in a presently preferred skewed manner such that pathways 90 provide a motor winding pathway that is offset from the rotor axis 92. The skew of laminations 86 may or may not correspond in some manner with the offset angle or changing offset angle of the row of magnets 82 and is not limited to the position shown in FIG. 2. A skewed stator 80 is also indicated in FIG. 2A which shows an offset path from axis 92 which field windings 88 travel through stator 80. The skewing angle or offset from the rotor axis is used to optimize performance. The skewing angle of stator 80 may be variable rather than fixed along its length. While skewed stator 80 is the presently preferred embodiment, other factors or combinations of factors (e.g. small air gap, magnet orientation, etc.), as discussed, produce excellent pump and motor performance without a skewed stator.

An axial force is produced on rotor 46 during rotation which can be varied by moving stator 80 axially along pump housing 12. Stator 80 is axially adjustable for this purpose and could be fixed in position during manufacturing for optimal performance given the number of magnets to be used and other factors discussed hereinafter. The axial force produced hereby can be used to offset thrust created during pumping to reduce the load on front or rear bearing assemblies 24 and 42, respectively, as desired. The axial positioning of stator 80 may also be used to optimize electrical motor efficiency.

Figure 5:
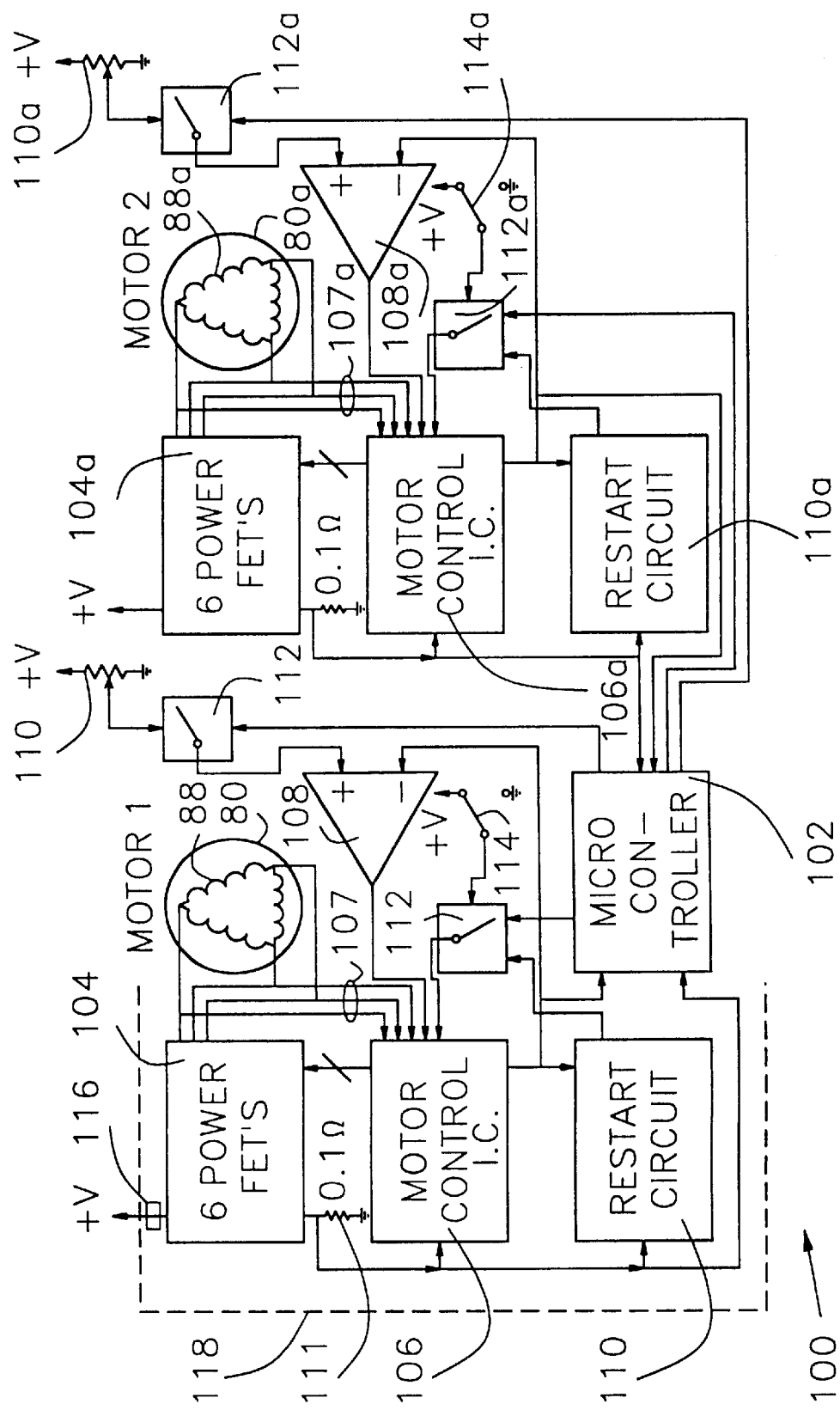
FIG. 5 is a block diagram of a control system including a back emf integrated circuit and a microprocessor.
Figure 10:
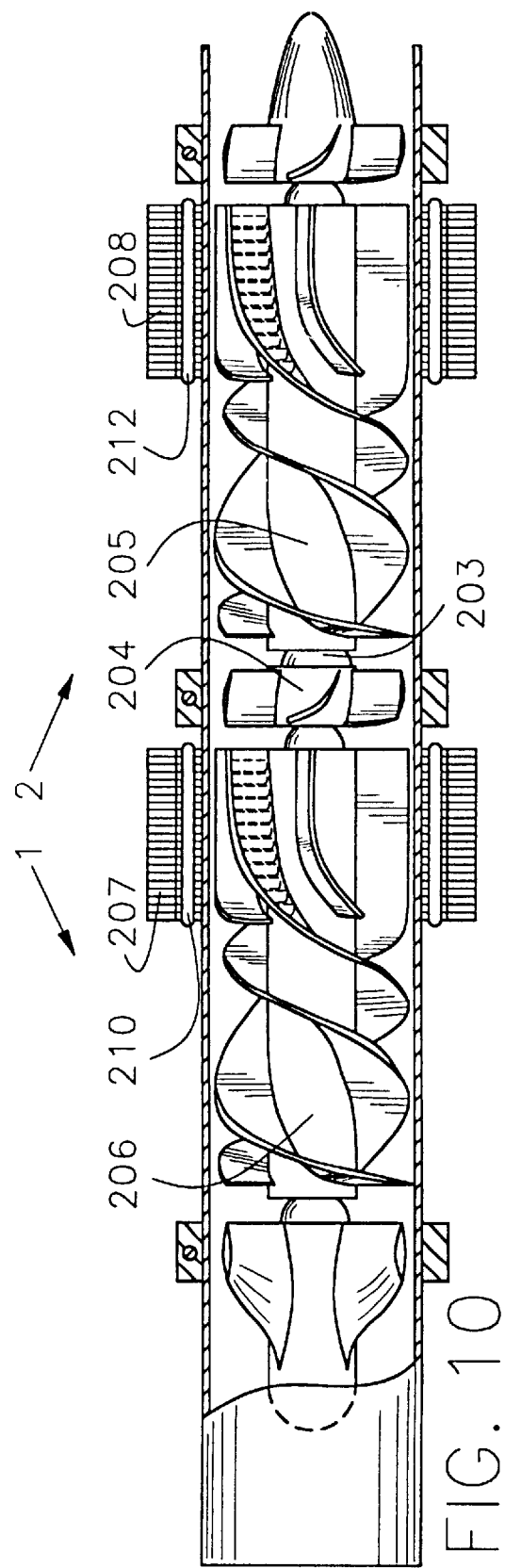
FIG. 10 is an elevational view, in section, of two axially spaced pumps for separate or combined operation in accord with the present invention.

Referring to FIG. 5, a block diagram of control system 100 of the present invention is shown. Note that control system 100 may operate two motors 1 and 2 such as shown in FIG. 10. For some applications either for implantation or for external use, it may be desirable to have two pumps connected either in parallel or series. Thus, control system 100 can be easily configured for this purpose if desired. In addition, magnets (not shown) may be placed in the inducer hub to provide a secondary motor in the case of primary motor or controller failure. Various other back-up and redundancy configurations may be used.

For instance, in an axially spaced pump configuration shown in FIG. 10, motors 1 and 2 are axially displaced from each other and may be operated separately or in conjunction with each other as control system 100 regulates power, as discussed hereinafter, to axially spaced stators 207 and 208 containing stator windings 210 and 212, respectively. Ball-socket bearing 203, or another bearing discussed hereinafter, on modified diffuser 204 rotatably supports rotor 205 of motor 2 which is axially spaced from rotor 206 of motor 1. Diffuser 204 acts as a flow straightener when independent operation of motor 2 is desired. Control system 100 may be used to operate both motors simultaneously or to turn one motor on if micro-controller 102 senses a motor has failed. Micro-controller 102 may be programmed for pulsatile motor operation or continuous speed motor operation of one or more motors, as desired.

If only one pump is to be used, extra components may be removed. In FIG. 5, except for micro-controller 102, most components are duplicated to allow operation of two motors. For convenience, reference to corresponding components will be made to one number with the corresponding component having an "a" suffix. Control system 100 operates either manually or by micro-control as discussed subsequently so it may be used for test purposes if desired.

Control system 100 applies current to stator windings 88. Preferably stator 80 includes three stator windings 88. Stator 80 generates a rotating magnetic field which rotor 46, containing magnets 82, follows to produce motion. The motor stator may be three phase "Y" or "Delta" wound. The operation of the brushless D.C. motor of the present invention requires a proper sequence of power to be applied to stator windings 88. Two stator windings 88 have power applied to them at any one time. By sequencing the voltage on and off to the respective stator windings 88, a rotating magnetic field is produced.

A preferred embodiment three-phase motor requires a repetitive sequence of six states to generate a rotating magnetic field but other commutation schemes could be used as well. The six states are produced by electronic commutation provided by power F.E.T.'s 104. If Motor 1 were sequenced through the six electrical states at a controlled frequency without feedback, its operation would be that of a stepper motor. In such a mode of operation, the motor rapidly loses its ability to generate torque as the rpm's increase.

Control system 100 detects back electromotive force or back emf to control motor operation. Whenever a conductor, such as field winding 88, is cut by moving magnetic lines of force, such as magnets 82, a voltage is induced. The voltage will increase with rotor speed. It is possible to sense this voltage in one of the three stator windings 88 because only two of the motor's windings are activated at any one time, determine rotor 46 position, and to activate commutator switches 104. The circuitry is much simpler and more reliable than Hall Effect sensors which have been used in the past. Although a back emf control is the presently preferred embodiment, a Hall effect driven commutation scheme could also be used.

Back emf integrated circuit 106 provides sensors for detecting the back emf from lines indicated at 107 and operates commutation switches 104 accordingly. A presently preferred back emf integrated circuit includes a ML4411 motor controller integrated circuit. Each commutation switch F.E.T. is preferably turned all the way on or off for maximum power efficiency.

Back emf integrated circuit 106 also provides start up mode operation when the back emf is not present or large enough for detection. From zero to approximately 200 rpm's, motor 1 operates in stepper motor fashion as described hereinbefore. Motor speed is controlled with difference amplifier 108 which may take its speed signal from either micro-controller 102 or speed adjust pot 110 as selected by switch 112. A speed detection signal is available from back emf integrated circuit 106 for this purpose.

Restart circuit 110 and micro-controller 102 monitor voltage developed across sense resistor 111 (present preference is about 0.1 ohms) and the frequency signal from back emf integrated circuit 106 to determine whether motor 1 should be restarted i.e. due to sudden increase or decrease in current or frequency. Switch 113 may be used to select between use of restart circuit 110, micro-controller 102, or a manual restart switch 114. Controller 102 may be programmed to produce an alarm signal if there are sudden changes in power consumption or frequency as may occur if heart strength weakens or improves. To protect the electronics from electromagnetic interference (EMI), ferrite beads 116 are used with wires to an external power supply. The electronics are preferably hermetically sealed in case 118 which is formed of a high mu material to limit EMI.

Referring now to FIG. 11 through FIG. 14B, there is shown a presently preferred bearing system embodiment 300 in accord with the present invention. While bearing system 300 is exemplified within an axial flow pump, it could also be used in a radial flow pump configuration, such as a centrifuge, or a mixed flow pump. The long life of the bearing system lends itself to use either in long-term implanted blood pumps or short-term external devices. While bearing system 300 is especially suited for blood pumps, it may also be used in fluid pumps or motors to reliably support high rotor speeds with little friction for long life. Preferably, bearing system 300 is comprised of ceramics, as discussed hereinafter. However, if wanted for particular conditions, bearing system 300 may comprise materials such as hardened metals.

Bearing system 300 is comprised of three basic components that include a shaft, an endstone, and an olive ring jewel. Representative elements in FIG. 11 disclose shaft 302, endstone 305, and olive hole ring jewel 307. In the presently preferred embodiment, bearing system 300 utilizes the same bearing components on front bearing assembly 309 as on rear bearing assembly 311 to thereby support both ends of a rotor, such as rotor 304. However, differences between front bearing assembly and rear bearing assembly are preferably designed to develop after break-in of bearing system 300, as discussed hereinafter. Front bearing assembly 309 and rear bearing assembly 311 may be mounted in the pump casing or to pump flow elements such as the diffuser, straightener, and the like discussed herein. Such mountings are referred to generally in FIG. 12 as component 301. Bearing components, such as endstone 305, could be monolithically formed within pump flow elements 301 if those elements are formed of the necessary materials.

Shaft 302 of bearing system 300 may comprise a solid shaft mounted or affixed through the rotor 304. Alternatively, shaft 302 may be comprised of two end sections that are mounted within appropriately sized but oppositely situated cavities in rotor 304. In FIG. 13, one of such shaft end segments is denoted as shaft end section 306. As well, shaft 302 may be monolithically constructed with rotor 304 or a portion thereof so that it forms a one piece unit.

Preferably, shaft 302 is comprised of zirconia, whereas endstone 305 and olive hole ring jewel 307 are preferably formed of sapphire. The fact that sapphire is a somewhat harder material than zirconia is used to advantage as discussed subsequently.

In the presently preferred embodiment of shaft 302, radiused end surfaces 308 and 310 are formed on front and rear bearing assemblies 309 and 311, respectively. The remainder of shaft 302 is preferably cylindrical along its length but could have tapering portions or portions with other cross-sectional shapes. Because the sapphire material forming endstone 305 is somewhat harder than the zirconia of shaft 302, radiused surface 308 in front bearing 309 wears but endstone 305 experiences substantially no wear. Designing the bearing system to wear only on radiused surface 308 is preferable because this design results in less friction after break-in as compared to designing wear to occur on endstone 305, or on both endstone 305 and radiused surface 308. Furthermore, because front bearing assembly 309, rather than rear bearing assembly 311, supports the thrust load, rear bearing assembly 311 experiences little wear.

The radius of curvature R1 indicated in FIG. 11 of radiused end surface, such as surface 308 as compared to the radius of curvature R2 of the circumference 312 as shown in FIG. 12 is preferably about three to one. However, any ratio larger than about one to one could be used. The selection of the radius of curvature R1 in this manner provides that the wear occurs very quickly during initial break-in. In fact, referring to FIG. 14, rapid wear begins almost immediately during initial rotation at contact point 318 on radiused surface 308 of shaft end section 302 of front bearing assembly 309. Wear then tapers off essentially to zero wear once bearing surface area 320 becomes large enough to support the thrust load. In other words, true point contact occurs during initial bearing operation of front bearing 309, but wear of radiused surface 308 results in a small flat or bearing surface area 320 after an initial break-in period to effect a near point contact.

While the surface area of point contact 318 between radiused surface 308 and endstone 305 may have an area with a diameter of a few angstroms, the diameter D1 of the wear flat or bearing surface 320 is preferably less than about twenty-five thousandths (0.025) of an inch. Since little, if any, axial load is placed on rear bearing assembly 311, little, if any, wear occurs on the radiused shaft end 310. This is one distinction between front and rear bearing assemblies 309 and 311, respectively.

The selection of the radius of curvature R1 also affects the change in end-play E1 of shaft 302, shown proportionately overly large in FIG. 12. The change in end-play E1 between before and after break-in is indicated at least somewhat more proportionately in FIG. 14A and FIG. 14B, where the width of the end portion that is worn off to create wear flat or bearing surface 320 is about the same as the line width designated as E1. Preferably, change E1 is designed to be less than five thousandths (0.005) of an inch. As suggested by FIG. 14A that presents a greatly enlarged view of shaft 302, change E1 is a relatively small change in axial play. It will be understood that increasing the radius of curvature R1 will produce the necessary size bearing surface area 320 to support axial thrust with a relatively smaller change E1 in end-play of shaft 302. Thus, the overall change in length of shaft 302 due to wear is minimized by using a shaft end radius R1 significantly larger than shaft radius of circumference R2. This results in extremely stable shaft end-play and axial clearances between pump components throughout the life of the pump. Stable shaft end-play maintains low levels of blood clotting and damage. Preferably, the shaft end-play after break-in is less than ten thousandths (0.010) of an inch.

The purpose of rear endstone 322 is mainly to secure and minimize impeller movement during handling and due to patient mobility. Rear endstone 322 therefore completes bearing system 300 to provide a sturdy, precise, and simple assembly.

Olive hole ring jewels, such as jewel 307, may be commercially purchased or specially made. Olive hole ring jewels are normally used in components of precision instruments such as relatively slow moving visually readable needle indicators of analog meter movements such as volt meters, and the like. However, in a preferred embodiment of the present invention, olive hole ring jewel 307 is used to support high speed rotation of shaft 302 with very little friction. Olive hole ring jewel 307 has a doughnut-shaped or torroidial inner surface portion 330 that makes line contact, or near line contact, around circumference 312 of shaft 302 as indicated in cross-section in FIG. 12A. In FIG. 14A, cross-sectional points 319 and 321 of inner surface portion 330 contact shaft 302. Of course, points 319 and 321 lie on the circle indicated as circumference 312 of the cross-section shown in FIG. 12A.

Inner surface 330 also defines aperture 334 (see FIG. 11) that receives circumference 312 of shaft 302. Little bearing heat is produced because of the very low friction between zirconia shaft 302 and jewel 307 due to the near line contact that is made around the circumference 312 of shaft 302. The locus of the width of the near line contact, as measured parallel to the axis of rotor 304, is preferably less than about ten thousandths (0.010) of an inch.

Radial loads produced due to high speed rotation of rotor 304 are much smaller than axial loads so that virtually no wear occurs around zirconia rotor shaft 302. Even when the pump components were disassembled for inspection after significant running time, no wear could be detected during microscopic examination of shaft 302 where shaft 302 contacts olive hole ring jewel 307. The radial clearance between shaft 302 and olive hole ring jewel 307 is preferably in the range of about one ten-thousandths to two ten-thousandths (0.0001–0.0002) of an inch.

Olive hole ring jewel 307 maintains extremely precise impeller rotation and yet allows for axial shaft movement. No pre-load mechanism is required because bearing system 300 is designed to run with a small amount of shaft end-play. The shaft end-play after break-in is preferably less than about ten thousandths (0.010) of an inch. Fluid pressure is not needed to support bearing loads because the bearing loads at circumference 312 and inner curved surface 330 contact each other. This bearing system therefore eliminates the need for an external reservoir or complex fluid porting arrangements or other forced fluid methods as used with other bearing systems. Blood trauma and potential of clotting is therefore reduced as compared with bearing systems that force blood through small clearances.

Another feature of olive hole ring jewel 307 is a relatively narrow width W as indicated in FIG. 13 that permits heat conduction through olive hole ring jewel 307. Width W is measured parallel to axis of rotation of rotor 304. While commercially available olive hole ring jewels may be purchased with a width of less than thirty-five thousandths (0.035) of an inch, specially made jewels may be formed with an even smaller width as desired. The advantage of a small width W of olive ring jewel 307 is that the heat produced by bearing system 300 is not insulated by jewel 307 so as to continue increasing. Instead, the heat conducts outwardly into the blood to provide a cool running bearing. The lower bearing temperature reduces the likelihood of bearing seizure, increases bearing life, and reduces the possibility of thrombus formation when blood contacts the bearings. It will be observed that a minimum thickness of jewel 307 is preferably required to support radial forces acting on shaft 302 on circumference 312 and/or to maintain jewel 307 in contact with circumference 312 of shaft 302.

Bearing system 300 requires no shaft seals. Instead, the outer surfaces of shaft 302, endstone 305, and olive hole ring jewel 307, define void 332 as indicated in FIG. 14A and FIG. 14B. Void 332 may be made very small by selecting radius R1 to be significantly larger than radius R2. Any blood that enters void 332 coagulates quickly due to bearing heat to form a smooth and stable surface that conforms to radiused surface 308. Due to the conforming shape, coagulated blood does not interfere with shaft rotation. Once coagulated, the blood cannot leave void 332 to enter the blood stream. Furthermore, any coagulated blood in void 332 acts to further stabilize end play of shaft 302. Radius R2 of shaft 302 may be made quite small if desired to reduce even further any friction created by coagulated blood. Certain other advantages of a void such as void 332 over attempts to seal or wash bearings with saline fluids are discussed hereinafter in connection with other bearing embodiments. However, FIG. 11 through FIG. 14B disclose the presently preferred bearing system configuration embodiments.

In another bearing embodiment having a void for blood, FIG. 6A discloses a ball-socket bearing configuration. The bearings are comprised of bio-compatible material such as ceramic material. The ball-socket bearing 121 may be configured as shown in FIG. 1 or in other configurations. Ball 120 is preferably secured by some securing means such as glue, welding, or other means along edge 128. Ball 120 could be molded into one component or split and secured as is known in the art. Ball 120 has a spherical surface 122 that engages a mating seat spherical surface 124. A void or bearing chamber 126 is filled with bio-compatible material to prevent blood from coming into this area and stagnating. In this embodiment, bearing chamber 126 is left empty and allowed to fill with blood. The blood cross-links due to bearing heat and takes on a soft, pliable, plastic texture. The cross-linked blood may perform, to some extent, a bearing surface function. The cross-linked blood then prevents other blood from entering the bearing and stagnating.

In an alternative bearing configuration, shaft-journal bearing 130 provides that shaft 132 is secured to component 134, which may be rotor 46, for rotation with respect to a second component 136, which may be diffuser 20. Journal sleeve 138 has a cylindrical bearing receiving surface 140 for engaging cylindrical shaft bearing surface 142. Biocompatible material in bearing chamber 144 is preferably cross-linked blood, as discussed hereinbefore, which has leaked into this chamber, heated up, and solidified.

Another embodiment of a shaft-journal bearing would include a shaft (not shown) extending through rotor 46 and engaging respective sleeves on flow straightener 18 and diffuser 20. As well, the flow straightener and/or diffuser, or relevant portions thereof, may be made from a suitable material, such as zirconia, with the bearing surfaces being formed or machined directly into that material. In a similar manner, the bearing surfaces of bearing 121, 130, or other bearings could be machined into a bearing mount component in this way.

To avoid the problem of blood stagnation in the region of the bearing, several bearing washing configurations, using directed blood flow or pump differential pressures, may also be used as part of the present invention. Referring to FIG. 3, there is shown a means for using a pump pressure differential for washing bearing 150 which includes shaft 152 and journal sleeve 153. High pressure region 154 produces a blood flow through passage 156 to wash bearing 150 and exit to lower pressure region 158. Thus, blood is prevented from stagnating behind bearing 150.

Another bearing embodiment (not shown) would include a pressure fed journal bearing to form a hydrodynamic film that supports the shaft and loads so that the bearing surfaces do not touch. Shaft 152 would be slightly undersize with respect to a journal sleeve for this purpose, and a pressure fed flow passage may be directed through such a hydrodynamic journal bearing from high pressure region 154 to low pressure region 158.

FIG. 6C illustrates another bearing washing method by producing bend 160 in pump housing 12. This places bearing 162 in a high velocity flow area. Blood flow through bend 160 washes the bearing members which include a male portion 164 and mating member 166. Other configurations for this type arrangement may be used but the general principle is as shown. The flow straightener is removed in this embodiment but may be included in another embodiment where it does not necessarily need to act as a bearing support.

FIG. 6D and 6E illustrate yet another alternative bearing arrangement embodiment. In this embodiment, a bearing shaft 170 extends through journal sleeve 172. Bearing shaft 170 has an oblong, or substantially oval transverse cross-section as shown in FIG. 6E. This configuration produces flow paths 174 through journal sleeve 172 so as to flush the bearing and prevent blood stagnation. Shaft 170 could also be fluted so as to have spirals, slots, or in some other manner form flow paths 174 along its periphery within sleeve 172.

FIG. 6F shows a bearing configuration wherein rotor 46 is cantilevered with respect to diffuser 20 using two bearings 180 and 182. Shaft 184 extends between the two bearings. Each bearing includes a rotating ball surface, 186 and 188, mating with a socket surface 190 and 192, respectively. Socket surfaces 190 and 192 are formed in ceramic material sleeves 194 and 196, respectively. The bearings are "zero tolerance" bearings. Thus, either shaft 184 which runs through diffuser 20, or the diffuser 20 itself must provide a take up mechanism that keeps each ball surface 186 and 188 tightly engaged with respective socket surfaces 190 and 192. For this purpose, diffuser 20 could be made of compressible material. Alternatively, diffuser 20 could receive injection molding around sleeves 194 or 196.

As another alternative, either a passive or active, or a combination passive-active magnetic bearing suspension system (not shown) could be used to rotatably mount rotor 46 whereby rotor 46 would be axially positioned and/or bearing surfaces would be suspended with respect to each other using magnetic force.

The method of the present invention is illustrated in FIG. 8 which shows a test matrix for optimizing the pump parameters which are believed to affect hemolysis. This method enables optimization of pump parameters as discussed hereinafter with a minimum number of tests. Although this matrix is designed for a blood pump with no inducer or flow straightener, it is believed the method of the present invention is clearly illustrated with this example and may be used to improve most other blood pump designs with respect to hemolysis, thrombus, pump efficiency, cost, and other important factors. Using this approach, it is possible to thoroughly investigate many parameters in an organized, methodical approach to achieve highly desired goals such as optimum pump performance and minimum hemolysis.

To apply this method, it was first necessary to identify the pump parameters that were believed to affect hemolysis. The variables are listed at the headings of the test matrix and include blade tip shape, radial clearance, axial clearance, number of blades, and impeller length. To judge effectively the impact of each variable on hemolysis, the method of the present invention requires that all pump dimensions be held constant while only one variable is changed. As shown in the matrix of FIG. 8, 16 different tests are used. Preferably, each test is made at least three different times to provide statistical results and check consistency.

The information learned in initial tests is used later in the matrix. For example, tests 1 and 2 compare the effects of flat and round blade tip geometries. The least hemolytic of the two is then used in all remaining tests. If there is no statistically significant difference, then the result that provides superior hydrodynamic performance is used. If there is no hydrodynamic difference, then the least expensive parameter to manufacture is used. Test conditions are constant for each parameter. All tests were made using bovine blood at a flow of 5 liters/min against 100 mm Hg. The duration of each test was 20 minutes. The pump circulates blood through a test loop having a 500 cc blood reservoir which was conveniently a 500 cc blood bag. The 500 cc blood bag is preferably changed after each version of each parameter is tested.

In order to compare various impeller and stator blade geometries within a reasonable time period, a stereolithography technique was used to quickly realize the complex shapes. This technique relies on a laser beam that scans the surface of a liquid acrylic polymer. The polymer hardens under the influence of the laser, and layer by layer a solid shaped is formed from the liquid surface.

To compare hemolysis results, an index of hemolysis (IH) is used. This is defined as the amount of hemoglobin liberated in grams per 100 liters of blood pumped against 100 mm Hg. In equation form:

$$IH = \Delta Hb \times V \times (1 - Ht) \times \frac{100}{(\text{Flow} \times \text{Time})}, \quad (1)$$

where:

IH equals amount of hemoglobin liberated in grams per 100 liters of blood pumped against 100 mm Hg;

Ht is the hematocrit in decimal percent;

V is the blood volume in liters;

ΔHb is the amount of hemoglobin liberated in a fixed time period in grams/liter;

Flow is the flow rate in liters per minute; and

Time is the total time in minutes at that flow rate.

The final results are seen in the matrix of FIG. 8 and other more detailed factors of testing in accord with the method of this invention are discussed more thoroughly in the articles which have been named previously and incorporated herein by reference.

As to manufacturing and usage considerations, Pump 10 is preferably manufactured using materials designed to be buoyant inside the body to make the completed pump neutrally buoyant or approximately neutrally buoyant. This minimizes stress on stitches or other means used to position the pump within the body. Thus, the rotor, rotor blades, and/or other components may be made with lightweight material having sufficient thickness to produce a buoyant effect.

Pump 10 has numerous uses as a blood pump including use as a portable blood pumping unit for field service or for other clinical applications involving other fluids. It could, for instance, be used in a compact heart-lung machine. Due to the small volume and size of pump 10, it can be placed close to a patient to minimize shock caused when initiating blood pump operation using saline solution. Larger pumps, with larger volume, may be awkward to move close by a patient to eliminate this shock.

Thus, the blood pump of the present invention, optimized using the method of the present invention has many advantages over the prior art. For instance, there are no blood seals which require bearing purge systems. The bearing system has been found to require no maintenance for long-term, reliable operation. No Hall Effect sensors are required which may tend to limit motor control reliability due to their complexity. As well, pump 10 provides low power consumption and produces very low levels of hemolysis.

The foregoing disclosure and description of the invention is illustrative and explanatory thereof, and it will be appreciated by those skilled in the art, that various changes in the size, shape and materials as well as in the details of the illustrated construction, reliability configurations, or combinations of features of the various rotary pump elements of the present invention may be made without departing from the spirit of the invention.

What is claimed is:

1. A blood-pump bearing system for rotatably supporting a rotor section that is rotatable with respect to a housing through which blood is pumped, said bearing system comprising:

a shaft for rotatably supporting said rotor section, said shaft having a circumference defined by a first radius, said shaft terminating at a shaft end, said shaft end comprising a radiused surface defined by a second radius, said second radius being greater than said first radius;

an endstone mounted to said housing having a flat planar surface operable to contact said radiused surface of said shaft end;

a shaft circumferential bearing mounted to said housing and having an aperture therethrough for receiving said circumference of said shaft, said shaft circumferential bearing being operable to support radial loads acting on said shaft, said shaft circumferential bearing comprising a curved inner surface that defines said aperture, said curved inner surface being operable for making near line contact along said circumference of said shaft as said shaft rotates, wherein said shaft circumferential bearing comprises an olive hole ring jewel;

wherein a void is formed between said shaft end and said endstone into which pumped blood that leaks between said circumference of said shaft and said shaft circumferential bearing coagulates;

a plurality of individual magnets disposed on said rotor along a path that defines at least a portion of a helix; and a stator mounted to said housing.

2. The pump bearing system of claim 1, wherein:

said second radius is about three times said first radius.

3. The pump bearing system of claim 1, wherein:

said endstone is comprised of a first material, said shaft end is comprised of a second material of less hardness than said first material such that wear occurs on said radiused surface of said shaft end to produce a flat surface thereon.

4. The pump bearing system of claim 1, wherein:

said flat surface has a diameter less than about 0.025 inches.

5. The pump bearing system of claim 1, wherein:

said second radius is selected such that change of shaft axial end-play due to creation of said flat surface is less than about 0.005 inches.

6. The pump bearing system of claim 1, wherein:

said near line contact has a locus with a width of less than about 0.010 inches.

7. The pump bearing system of claim 1, wherein:

said olive hole ring jewel has a width as measured parallel to an axis of said shaft of less than about 0.035 inches to promote heat transfer through said olive hole ring jewel.

8. The pump bearing system of claim 1, wherein said shaft is axially movable to the extent that end-play of said shaft is less than about 0.010 inches.

9. The pump bearing system of claim 1, wherein radial clearance between said shaft circumferential bearing and said circumference of said shaft is about 0.0001–0.0002 inches.

* * * * *